United States Patent [19]
Dawson et al.

[11] Patent Number: 5,773,638
[45] Date of Patent: Jun. 30, 1998

[54] GELATION ADDITIVE FOR HYDRAULIC FRACTURING FLUIDS

[75] Inventors: Jeffrey C. Dawson, Spring; Hoang Van Le, Houston, both of Tex.

[73] Assignee: BJ Services Company, Houston, Tex.

[21] Appl. No.: 858,018

[22] Filed: May 16, 1997

Related U.S. Application Data

[63] Continuation of Ser. No. 502,352, Jul. 14, 1995, abandoned.

[51] Int. Cl.$^6$ .......................................................... C07F 7/00
[52] U.S. Cl. ................................. 556/51; 556/52; 507/271
[58] Field of Search .......................... 556/51, 52; 507/271

[56] References Cited

U.S. PATENT DOCUMENTS

| | | | |
|---|---|---|---|
| 4,210,206 | 7/1980 | Ely et al. | 166/294 |
| 4,464,270 | 8/1984 | Hollenbeak et al. | 252/8.55 R |
| 4,470,915 | 9/1984 | Conway | 252/8.55 R |
| 4,502,967 | 3/1985 | Conway | 252/8.55 R |
| 4,579,670 | 4/1986 | Payne | 252/8.55 R |
| 4,702,848 | 10/1987 | Payne | 252/8.551 |
| 4,883,605 | 11/1989 | Putzig | 252/8.551 |
| 4,885,103 | 12/1989 | Putzig et al. | 252/8.551 |
| 5,089,149 | 2/1992 | Ridland et al. | 252/8.551 |
| 5,145,590 | 9/1992 | Dawson | 252/8.551 |

FOREIGN PATENT DOCUMENTS

| | | |
|---|---|---|
| 0 092 756 | 11/1983 | European Pat. Off. . |
| 0743172 A1 | 11/1996 | European Pat. Off. . |
| 1093465 | 6/1966 | United Kingdom . |

OTHER PUBLICATIONS

Konunova, Ts. B., et al., "Study of the Complexing of Zirconium and Hafnium With Aldehydes and Ketones", *Chemistry of inorganic coordination compounds,* University of Kishinev, Kishinev, Russia, 1978.

PCT International Search Report.

Chemical Abstracts, vol. 90, No. 24, (Jun. 11, 1979) [Columbus, Ohio, U.S.]; Abstract No. 193278m; Konunova, Ts. B., et al., "Study of Zirconium and Hafnium Complexation With Aldehydes and Ketones".

*Primary Examiner*—Porfirio Nazario-Gonzalez
*Attorney, Agent, or Firm*—Arnold, White & Durkee

[57] ABSTRACT

A method of formulating an organo-zirconium compound is accomplished by combining in solution a dialdehyde such as glyoxal with zirconium carbonate. The reacting solution forms an organo-zirconium compound and carbon dioxide which is evolved as a gas from the solution. This eliminates the need to filter or wash the organo-zirconium compound in order to remove undesirable by-products. The organo-zirconium compound can be used as a crosslinking agent for crosslinking aqueous polymer gels used in fracturing fluids for fracturing subterranean formations of oil and gas wells.

31 Claims, No Drawings

GELATION ADDITIVE FOR HYDRAULIC FRACTURING FLUIDS

This is a continuation of application Ser. No. 08/502,352, filed Jul. 14, 1995, now abandoned.

BACKGROUND OF THE INVENTION

1. Field of the Invention

This invention relates to a method of forming an organo-metallic compound, and particularly to an organo-zirconium compound, from a starting material of zirconium carbonate, and to a method of use of such an organo-zirconium compound in crosslinking gelled fracturing fluids used in treating subterranean formations of oil and gas wells.

2. Description of the Prior Art

Hydraulic fracturing fluids used in fracturing subterranean formations of oil and gas wells are usually formed from aqueous based fluids which are gelled by the addition of soluble polymers. These soluble polymers are often formed from solvatable polysaccharides which include such things as guar, guar derivatives and carboxylated cellulose. With very little addition of these polymers, the viscosity of the aqueous fluid can be increased dramatically. Increasing the viscosity of these aqueous based fluids for use as fracturing fluids is beneficial for various reasons. High viscosity fluids create better, larger fractures within the formation when introduced under high pressure. The higher viscosity fluids are also better able to carry proppants which are dispersed throughout the fluid and forced into the fractures so that the fractures remain open after the fluid is removed.

Typically, less than 1% by weight of the soluble polymers are added to water to form these viscous aqueous fluids. At 0.5% polymer concentration, water viscosity can be increased from about 1 cps to about 35 cps at 511 sec$^{-1}$ as measured using a Fann 50 viscometer. Further enhancement of the fluid viscosity occurs by the addition of crosslinking agents. These additives are able to bind polymer strands together to form a continuous network, thus further increasing the viscosity of the fluid. With the addition of these crosslinker additives, the viscosity of the aqueous fluids can be increased and exceed 500 cps at 170 sec$^{-1}$. These crosslinkers are generally formed using metal complexes of titanium, zirconium, aluminum or boron. The ligands associated with these metals are chosen so that once the complex is added to the aqueous polymer sol, the polymer must compete with the ligand for the metal. This is beneficial in that it ensures that the metal complex is homogeneously mixed in the polymer sol before crosslinking occurs. The delayed effect also results in less friction or back pressures while pumping the fluid at higher rates into the oil and gas wells.

Zirconium lactate is commonly used as a metallic crosslinker in crosslinking these aqueous polymer fluids. Zirconium lactate can provide delayed gelation and high viscosities at elevated temperatures for periods of time that are practical for hydraulic fracturing treatments in oil and gas wells. Prior art methods of formulating zirconium lactate typically involve mixing lactic acid to either zirconium hydroxychloride or zirconium oxychloride. These compounds react to form zirconium lactate as a white precipitate. To remove chloride by-products, the zirconium lactate product is filtered, washed and redissolved by neutralization with a suitable base. The base is generally sodium, potassium or ammonium hydroxide. This method of formulating zirconium crosslinkers has disadvantages, however. Washing and filtering of the zirconium lactate product usually results in less than 100% yield. As much as 10% Zr, measured as $ZrO_2$, may be lost during washing. Wastewater from the washings must be recovered and disposed of properly. The crosslinkers formed in this manner may be polymer specific and difficult to use with other polymers, in particular guar gum. These crosslinkers are also expensive because of the extensive processing and handling of wastewater that is required.

A need exists, therefore, for a new organo-zirconium compound for use as a crosslinker for polysaccharide containing fracturing fluids which overcomes many of the difficulties associated with the prior art zirconium lactate compounds.

A need also exists for such a new organo-zirconium compound which can be simply and inexpensively manufactured from commonly available starting materials.

A need also exists for a simple method of manufacturing an organo-zirconium compound which does not generate waste or loss of product as a result of washing and separating techniques.

A need also exists for such an organo-zirconium compound which is capable of more effectively crosslinking guar based aqueous fracturing fluids.

SUMMARY OF THE INVENTION

An organo-zirconium compound is formulated by combining in solution an amount of an aldehyde or dialdehyde with an amount of a zirconium salt. Most preferably, the aldehyde is selected from the group consisting of dialdehydes having about 2–4 carbon atoms, keto aldehydes having about 3–4 carbon atoms, hydroxyl aldehydes having 2–4 carbon atoms, ortho substituted aromatic dialdehydes and ortho substituted aromatic hydroxyl aldehydes. The most preferred reactants are zirconium carbonate and glyoxal with the molar ratio of zirconium to glyoxal being in the range from about 1:0.5 to 1:20, most preferably about 1:2.5 to 1:7.

The solution of glyoxal and zirconium carbonate is allowed to react with carbon dioxide being given off as a by-product. The carbon dioxide is allowed to evolve from the solution as a gas so that the zirconium product does not need to be washed to remove undesirable by-products.

The zirconium compound produced can be used as a crosslinking agent for crosslinking viscous polymer gels, such as those used in fracturing fluids. By further neutralizing the aqueous solution, zirconium precipitate is dissolved in solution. The solution can then be added to the polymer fluid.

The novel features believed characteristic of the invention are set forth in the appended claims. The invention itself however, as well as a preferred mode of use, further objects and advantages thereof, will best be understood by reference to the following detailed description of an illustrative embodiment.

DETAILED DESCRIPTION OF THE PREFERRED EMBODIMENT

A zirconium compound of the invention can be formed in a simple process by the addition of a zirconium salt to an aqueous solution of a selected aldehyde or dialdehyde. Suitable zirconium salts include carbonate, ammonium carbonate, oxychloride, acetate, tetrachloride and o-sulfate. The preferred salt is zirconium carbonate due to the nature of the by-products produced, as will be more fully described.

The aldehyde or dialdehyde (sometimes referred to collectively hereafter as "aldehyde") which is reacted with the zirconium salt is preferably selected from the group consisting of dialdehydes having 2–4 carbon atoms, keto aldehydes having about 3–4 carbon atoms, hydroxyl aldehydes having 2–4 carbon atoms, ortho substituted aromatic dialdehydes and ortho substituted aromatic hydroxyl aldehydes. Preferred aldehydes and dialdehydes include, for example, glyoxal, propane dialdehyde, 2-keto propanal, 1,4-butanedial, 2-keto butanal, 2,3-butadione, phthaldehyde, salicaldehyde, etc. The most preferred co-reactant is glyoxal, a dialdehyde, due to its ready availability from a number of commercial sources.

The zirconium carbonate is preferably reacted with the glyoxal in a molar ratio of zirconium ion to glyoxal in the range from about 1:0.5 to 1:20, most preferably in the range from about 1:2.5 to 1:7.

The process can be initiated by adding the zirconium carbonate to an aqueous solution of 40% aqueous glyoxal. Because zirconium carbonate is used, the reaction results in a by-product of carbon dioxide. Thus, during the reaction, carbon dioxide is given off as a gas which simply bubbles out of solution so that filtering and washing of the zirconium product is unnecessary. A precipitate is immediately observed. The aqueous glyoxal solution is very acidic, normally with a pH of about 2.5. At low pH, the zirconium product formed appears as a precipitate. If desired, this precipitate can be removed from solution by filtering and dried for later use.

By further neutralizing the solution with a suitable base, the zirconium precipitate can be dissolved and used as a crosslinking additive for crosslinking various viscous aqueous gels used as fracturing fluids. The solids can be slowly dissolved by neutralizing with base and heating from about 30 minutes to about 6 hours. The preferred temperature for heating can range from ambient to about 250° F. The most preferred heating temperature is about 200° F. for at least two hours.

The base can be added while the solution is still hot or after cooling. After the addition of base, the solution can be cooled or heating can continue. Preferred bases to use for neutralization include the alkali metal hydroxides such as potassium hydroxide or sodium hydroxide. Other bases include the alkanolamines, ammonium hydroxide and alkali metal carbonates and bicarbonates. The most preferred base is potassium hydroxide.

The preferred procedure used to make the crosslinker and its performance are described in the non-limiting examples which follow:

Example 1

An aqueous solution of 40%(wt) glyoxal weighing 44.25 gr. was heated to 200° F. Then, 20.0 gr. of zirconium carbonate (40.4% $ZrO_2$) slurried in 20.0 gr. of DI water was slowly added to the glyoxal solution and stirred for 60 minutes. During that time, 30.0 gr of water was added to help suspend the solids. After the 60 minutes, 25.24 gr. of 46% aqueous potassium hydroxide was slowly added to the slurry. The heating continued at 200° F. for another 120 minutes. During this time, the solids slowly dissolved. The dark colored solution was then cooled to ambient. The zirconium content measured as $ZrO_2$ is 5.5% and the pH was 5.55.

Example 2

A liter of tap water was treated with 20.0 gr. of technical grade potassium chloride to produce a 2% weight per volume (wt/vol) potassium chloride solution. Then, with agitation, 4.8 gr. of a fracturing fluid quality guar gum was added, together with 1.2 gr. of sodium bicarbonate, and hydrated for 60 minutes. Afterward, an aliquot of 250 ml of sol was taken and treated with 0.3 gr sodium thiosulfate and 0.06 ml of 50%(wt) monoethanolamine. Lastly, 0.1 ml of crosslinker prepared in Example 1 was added to the sol and stirred vigorously for 60 seconds. The pH of the sol was 8.85.

For the testing, a Fann 50 viscometer(Baroid Testing Equipment) with an R1B5 bob and cup were used. A sample of 48.0 gr was poured into the viscometer cup. The cup was screwed onto the viscometer and pressured to 200 psi with $N_2$. The sample was then continuously sheared at 42 $sec^{-1}$ while heating to 250° F. At temperature, a rate sweep using 105, 84, 63 and 42 $sec^{-1}$ was made and repeated every 30 minutes. The interim rate between the sweeps was 42 $sec^{-1}$. The stresses corresponding to each rate of the rate sweep, together with the rates, were converted to their logarithmic value. The Power Law indices, n' and K, were then determined as described by the American Petroleum Institute's bulletin RP-39. The n' values presented in Tables 1–14 are unitless whereas the K values have the units of $dyne/cm^2$-sec. The Power Law indices were then used to calculate the gel's viscosity at 105, 85 and 42 $sec^{-1}$. These data, over time, are shown in Table 1.

TABLE 1

Temperature (°F.) 250
Additives: 2% KCl, 4.8 gr. guar gum, 0.3 gr. $Na_2S_2O_3.5H_2O$, 0.06 ml 50% (wt) monoethanol amine, and 0.1 ml crosslinker
pH: 8.85

| | | | | Viscosity at Rates in $Sec^{-1}$ | | |
|---|---|---|---|---|---|---|
| TIME | TEMP | n' | K' | 105s-1 | 85s-1 | 42s-1 |
| 29 | 246 | 0.740 | 13.791 | 411 | 434 | 522 |
| 60 | 247 | 0.691 | 15.471 | 367 | 392 | 487 |
| 91 | 248 | 0.664 | 14.889 | 312 | 335 | 424 |
| 122 | 248 | 0.652 | 14.447 | 286 | 308 | 393 |
| 152 | 248 | 0.671 | 12.524 | 271 | 290 | 366 |
| 183 | 248 | 0.680 | 11.151 | 251 | 269 | 337 |
| 214 | 248 | 0.714 | 9.103 | 241 | 255 | 313 |
| 245 | 248 | 0.715 | 8.506 | 226 | 240 | 293 |

Example 3

The testing of the fluids described in the Examples 3–15 are conducted as stated in Example 2.

Another 250 ml aliquot of sol prepared in Example 2 was treated with 0.3 gr of sodium thiosulfate and 0.08 ml of 45%(wt) aqueous potassium carbonate. Then, 0.1 ml of crosslinker prepared in Example 1 was added with vigorous stirring for 60 sec. The pH of the sol was 8.83 and the data from the Theological evaluation are shown in Table 2.

TABLE 2

Temperature (°F.): 250
Additives: 2% KCl, 4.8 gr. guar gum, 0.3 gr. $Na_2S_2O_3.5H_2O$, 0.08 ml 45% (wt) $K_2CO_3$ and 0.1 ml crosslinker
pH: 8.83

| | | | | Viscosity at Rates in $Sec^{-1}$ | | |
|---|---|---|---|---|---|---|
| TIME | TEMP | n' | K' | 105s-1 | 85s-1 | 42s-1 |
| 34 | 248 | 0.676 | 21.613 | 478 | 512 | 644 |
| 65 | 248 | 0.665 | 18.521 | 390 | 418 | 530 |
| 96 | 248 | 0.641 | 18.057 | 340 | 366 | 472 |
| 126 | 248 | 0.665 | 14.958 | 315 | 338 | 428 |
| 157 | 248 | 0.663 | 13.684 | 285 | 306 | 388 |

TABLE 2-continued

Temperature (°F.): 250
Additives: 2% KCl, 4.8 gr. guar gum, 0.3 gr. $Na_2S_2O_3.5H_2O$, 0.08 ml 45% (wt) $K_2CO_3$ and 0.1 ml crosslinker
pH: 8.83

| TIME | TEMP | n' | K' | Viscosity at Rates in $Sec^{-1}$ | | |
|---|---|---|---|---|---|---|
| | | | | 105s-1 | 85s-1 | 42s-1 |
| 188 | 248 | 0.670 | 12.760 | 275 | 295 | 372 |
| 219 | 248 | 0.742 | 8.532 | 257 | 271 | 325 |
| 249 | 248 | 0.727 | 8.423 | 236 | 250 | 304 |
| 277 | 248 | 0.709 | 8.6484 | 223 | 237 | 291 |

Example 4

The Example 3 was repeated except that the potassium carbonate buffer was reduced to 0.02 ml and the crosslinker increased to 0.12 ml. The sol pH was 8.55. These test data are shown in Table 3.

TABLE 3

Temperature (°F.): 250
Additives: 2% KCl, 4.8 gr. guar gum, 0.3 gr. $Na_2S_2O_3.5H_2O$, 0.02 ml 45% (wt) $K_2CO_3$ and 0.12 ml crosslinker
pH: 8.55

| TIME | TEMP | n' | K' | Viscosity at Rates in $Sec^{-1}$ | | |
|---|---|---|---|---|---|---|
| | | | | 105s-1 | 85s-1 | 42s-1 |
| 34 | 248 | 0.585 | 35.220 | 510 | 557 | 747 |
| 64 | 248 | 0.613 | 27.269 | 450 | 489 | 642 |
| 95 | 248 | 0.618 | 23.132 | 391 | 424 | 555 |
| 126 | 248 | 0.632 | 19.179 | 346 | 374 | 485 |
| 156 | 248 | 0.634 | 16.792 | 306 | 330 | 428 |
| 187 | 248 | 0.623 | 15.897 | 275 | 298 | 388 |
| 218 | 248 | 0.621 | 15.0486 | 258 | 279 | 365 |
| 249 | 248 | 0.64 | 12.6557 | 237 | 256 | 330 |
| 276 | 248 | 0.697 | 8.6348 | 211 | 225 | 278 |

Example 5

In this next example, a 250 ml aliquot was treated with 0.3 gr of sodium thiosulfate and 0.05 ml of 45%(wt) potassium carbonate. Afterwards, 0.12 ml of crosslinker prepared in Example 1 was added to the vigorously stirred sol. The sol pH was 8.81 and the rheological data obtained at 250° F. are presented in Table 4.

TABLE 4

Temperature (°F.): 250
Additives: 2% KCl, 4.8 gr. guar gum, 0.3 gr. $Na_2S_2O_3.5H_2O$, 0.05 ml 45% (wt) $K_2CO_3$ and 0.12 ml crosslinker
pH: 8.81

| TIME | TEMP | n' | K' | Viscosity at Rates in $Sec^{-1}$ | | |
|---|---|---|---|---|---|---|
| | | | | 105s-1 | 85s-1 | 42s-1 |
| 34 | 248 | 0.337 | 43.733 | 200 | 230 | 367 |
| 62 | 248 | 0.659 | 24.222 | 495 | 532 | 677 |
| 92 | 248 | 0.622 | 23.972 | 413 | 447 | 584 |
| 123 | 249 | 0.586 | 25.954 | 378 | 412 | 552 |
| 154 | 248 | 0.554 | 26.897 | 337 | 371 | 508 |
| 185 | 249 | 0.884 | 5.4826 | 320 | 327 | 355 |
| 216 | 249 | 0.699 | 10.1253 | 249 | 266 | 329 |
| 247 | 248 | 0.689 | 9.6167 | 226 | 242 | 301 |
| 278 | 249 | 0.728 | 7.5082 | 212 | 224 | 272 |
| 309 | 248 | 0.73 | 6.8318 | 194 | 206 | 249 |

TABLE 4-continued

Temperature (°F.): 250
Additives: 2% KCl, 4.8 gr. guar gum, 0.3 gr. $Na_2S_2O_3.5H_2O$, 0.05 ml 45% (wt) $K_2CO_3$ and 0.12 ml crosslinker
pH: 8.81

| TIME | TEMP | n' | K' | Viscosity at Rates in $Sec^{-1}$ | | |
|---|---|---|---|---|---|---|
| | | | | 105s-1 | 85s-1 | 42s-1 |
| 340 | 249 | 0.760 | 5.643 | 185 | 194 | 230 |
| 370 | 249 | 0.750 | 5.636 | 176 | 186 | 221 |
| 401 | 249 | 0.769 | 5.073 | 173 | 182 | 214 |
| 432 | 249 | 0.773 | 4.687 | 163 | 171 | 201 |
| 463 | 249 | 0.779 | 4.290 | 153 | 161 | 188 |
| 493 | 249 | 0.770 | 4.312 | 148 | 155 | 183 |
| 524 | 249 | 0.748 | 4.612 | 143 | 151 | 180 |
| 554 | 249 | 0.780 | 3.825 | 137 | 144 | 168 |
| 585 | 249 | 0.744 | 4.837 | 147 | 155 | 186 |
| 616 | 249 | 0.763 | 4.630 | 154 | 162 | 191 |
| 647 | 249 | 0.757 | 4.560 | 147 | 155 | 184 |
| 678 | 249 | 0.727 | 4.848 | 136 | 144 | 175 |
| 709 | 249 | 0.725 | 4.453 | 124 | 131 | 159 |
| 740 | 249 | 0.775 | 3.263 | 114 | 120 | 141 |
| 771 | 249 | 0.748 | 3.325 | 103 | 109 | 130 |
| 802 | 249 | 0.733 | 3.192 | 92 | 97 | 118 |
| 832 | 249 | 0.793 | 2.231 | 85 | 89 | 103 |
| 863 | 249 | 0.754 | 2.442 | 78 | 82 | 97 |
| 894 | 95 | 0.542 | 18.5404 | 220 | 242 | 335 |

Example 6

Another 250 ml aliquot of sol described in Example 2 was treated with 0.30 gr sodium thiosulfate and 0.08 ml of 45%(wt) potassium carbonate. Then, 0.12 ml of crosslinker described in Example 1 was added to the vigorously stirred sol. The sol pH was 9.00 and the rheological data obtained at 250° F. is presented in Table 5.

TABLE 5

Temperature (°F.): 250
Additives: 2% KCl, 4.8 gr. guar gum, 0.30 gr. $Na_2S_2O_3.5H_2O$, 0.08 ml 45% (wt) $K_2CO_3$ and 0.12 ml crosslinker
pH: 9.00

| TIME | TEMP | n' | K' | Viscosity at Rates in $Sec^{-1}$ | | |
|---|---|---|---|---|---|---|
| | | | | 105s-1 | 85s-1 | 42s-1 |
| 34 | 248 | 0.542 | 63.259 | 751 | 827 | 1142 |
| 65 | 249 | 0.541 | 60.143 | 710 | 783 | 1082 |
| 96 | 248 | 0.522 | 60.192 | 651 | 720 | 1008 |
| 126 | 248 | 0.500 | 61.778 | 603 | 670 | 953 |
| 157 | 248 | 0.498 | 59.425 | 575 | 639 | 910 |
| 188 | 249 | 0.482 | 60.0358 | 539 | 601 | 866 |
| 219 | 248 | 0.469 | 60.4491 | 511 | 571 | 831 |
| 250 | 248 | 0.483 | 54.9207 | 495 | 552 | 795 |
| 281 | 248 | 0.479 | 54.3202 | 481 | 537 | 775 |
| 312 | 249 | 0.482 | 51.2398 | 460 | 513 | 739 |
| 343 | 249 | 0.475 | 50.945 | 443 | 494 | 716 |
| 374 | 249 | 0.477 | 48.841 | 428 | 478 | 692 |
| 404 | 249 | 0.472 | 48.797 | 418 | 467 | 678 |
| 435 | 249 | 0.485 | 44.742 | 407 | 454 | 653 |
| 444 | 249 | 0.480 | 45.127 | 401 | 448 | 646 |
| 475 | 249 | 0.471 | 46.581 | 397 | 444 | 645 |
| 506 | 249 | 0.468 | 45.321 | 381 | 426 | 620 |
| 537 | 249 | 0.473 | 44.167 | 380 | 425 | 616 |
| 567 | 249 | 0.483 | 41.667 | 376 | 419 | 603 |
| 598 | 248 | 0.465 | 44.375 | 368 | 412 | 601 |
| 629 | 248 | 0.470 | 42.310 | 359 | 402 | 584 |
| 660 | 248 | 0.476 | 39.888 | 348 | 389 | 563 |
| 691 | 248 | 0.476 | 38.688 | 338 | 377 | 546 |
| 722 | 248 | 0.489 | 35.133 | 326 | 363 | 520 |
| 753 | 248 | 0.474 | 36.299 | 314 | 351 | 508 |
| 784 | 248 | 0.478 | 35.062 | 309 | 345 | 498 |

TABLE 5-continued

Temperature (°F.): 250
Additives: 2% KCl, 4.8 gr. guar gum, 0.30 gr. Na$_2$S$_2$O$_3$.5H$_2$O, 0.08 ml 45% (wt) K$_2$CO$_3$ and 0.12 ml crosslinker
pH: 9.00

| TIME | TEMP | n' | K' | Viscosity at Rates in Sec$^{-1}$ | | |
|---|---|---|---|---|---|---|
| | | | | 105s-1 | 85s-1 | 42s-1 |
| 815 | 248 | 0.480 | 33.105 | 294 | 329 | 474 |
| 845 | 98 | 0.456 | 63.1739 | 502 | 584 | 827 |

Example 7

In this example, a liter of 2%(wt/vol) aqueous potassium chloride was vigorously stirred while adding 4.8 gr of fracturing fluid quality carboxymethylhydroxypropyl guar (CMHPG), a dual derivatized guar gum. Afterward, 1.2 gr of sodium bicarbonate was added as a buffer to accelerate polymer hydration. After adequate dispersing, the stirring rate was slowed and the polymer was allowed to hydrate for about an hour.

Then, as in the preceding examples, a 250 ml aliquot was withdrawn and treated with 0.45 gr of sodium thiosulfate. Next, acetic acid was added dropwise until the sol pH declined to 5.70. Afterward, 0.19 ml of crosslinker, prepared in Example 1, was added with vigorous stirring to the sol. The final pH of the fluid was 5.70 and 45.0 gr of the sol was poured into the Fann 50 cup. The rheological evaluation was conducted at 250° F. and as described in Example 2. These data are presented in Table 6.

TABLE 6

Temperature (°F.): 250
Additives: 2% KCl, 4.8 gr. CMHPG, 1.2 gr. NaHCO$_3$, 0.45 gr. Na$_2$S$_2$O$_3$.5H$_2$O, acetic acid added to adjust pH and 0.19 ml crosslinker
pH: 5.70

| TIME | TEMP | n' | K' | Viscosity at Rates in Sec$^{-1}$ | | |
|---|---|---|---|---|---|---|
| | | | | 105s-1 | 85s-1 | 42s-1 |
| 32 | 248 | 0.579 | 56.054 | 790 | 864 | 1162 |
| 61 | 248 | 0.557 | 46.181 | 588 | 645 | 882 |
| 90 | 248 | 0.507 | 40.588 | 409 | 454 | 643 |
| 119 | 248 | 0.504 | 29.040 | 289 | 321 | 455 |
| 148 | 248 | 0.520 | 20.366 | 218 | 241 | 339 |
| 177 | 249 | 0.551 | 12.402 | 153 | 169 | 232 |
| 206 | 248 | 0.560 | 8.259 | 107 | 117 | 159 |
| 235 | 248 | 0.562 | 7.043 | 92 | 101 | 137 |
| 263 | 248 | 0.530 | 5.347 | 60 | 66 | 92 |
| 292 | 248 | 0.529 | 4.430 | 49 | 55 | 76 |
| 321 | 248 | 0.591 | 2.475 | 37 | 40 | 54 |
| 350 | 248 | 0.428 | 4.082 | 28 | 32 | 48 |
| 379 | 248 | 0.408 | 3.689 | 23 | 27 | 40 |
| 408 | 248 | 0.456 | 2.686 | 21 | 24 | 35 |
| 432 | 249 | 0.516 | 1.856 | 20 | 22 | 30 |
| 461 | 249 | 0.420 | 2.458 | 17 | 19 | 28 |
| 490 | 249 | 0.363 | 2.642 | 14 | 16 | 24 |
| 519 | 248 | 0.364 | 2.339 | 12 | 14 | 22 |
| 548 | 248 | 0.439 | 1.506 | 11 | 12 | 18 |
| 577 | 248 | 0.440 | 1.382 | 10 | 11 | 17 |
| 606 | 248 | 0.400 | 1.461 | 9 | 10 | 16 |
| 635 | 248 | 0.265 | 2.462 | 8 | 9 | 16 |
| 663 | 248 | 0.548 | 1.239 | 8 | 9 | 15 |
| 693 | 248 | 0.207 | 2.882 | 7 | 9 | 15 |
| 722 | 248 | 0.166 | 3.338 | 7 | 8 | 15 |
| 751 | 248 | 0.239 | 2.416 | 7 | 8 | 14 |
| 780 | 248 | 0.268 | 2.136 | 7 | 8 | 14 |
| 809 | 248 | 0.276 | 2.070 | 7 | 8 | 14 |
| 838 | 100 | 0.672 | 0.513 | 11 | 12 | 15 |

Example 8

In this example, another 250 ml aliquot was withdrawn from the stock solution prepared as described in Example 2. This sol was treated with 0.3 gr of sodium thiosulfate and 0.10 gr of fumaric acid. The sol pH, after dissolution of the acid, was 5.70. Lastly, with vigorous stirring of the sol, 0.38 ml of crosslinker prepared in Example 1 was added. The sol pH was 5.57 and the data from the rheological evaluation at 250° F. is presented in Table 7.

TABLE 7

Temperature (°F.): 250
Additives: 2% KCl, 4.8 gr. guar gum, 0.3 gr. Na$_2$S$_2$O$_3$.5H$_2$O, 0.10 gr. fumaric acid and 0.38 ml crosslinker
pH: 5.57

| TIME | TEMP | n' | K' | Viscosity at Rates in Sec$^{-1}$ | | |
|---|---|---|---|---|---|---|
| | | | | 105s-1 | 85s-1 | 42s-1 |
| 32 | 248 | 0.708 | 19.068 | 490 | 521 | 640 |
| 60 | 249 | 0.689 | 15.292 | 360 | 384 | 478 |
| 89 | 251 | 0.760 | 6.962 | 228 | 240 | 284 |
| 118 | 251 | 0.786 | 3.731 | 138 | 144 | 168 |
| 147 | 251 | 0.724 | 3.238 | 90 | 95 | 115 |

Example 9

Another 250 ml aliquot was withdrawn from the stock solution prepared as described in Example 2. The sol was treated with 0.3 gr sodium thiosulfate and 0.5 ml of a 45%(wt) solution of potassium carbonate. The crosslinker prepared in Example 1 was diluted to 50%(wt) with tap water. Then, with vigorous stirring of the sol, 0.25 ml of the diluted crosslinker was added. The sol pH was 8.50 and the data for the rheological evaluation at 200° F. is presented in Table 8.

TABLE 8

Temperature (°F.): 200
Additives: 2% KCl, 4.8 gr. guar gum, 0.3 gr. Na$_2$S$_2$O$_3$.5H$_2$O, 0.5 ml 45% (wt) K$_2$CO$_3$ and 0.25 ml of diluted crosslinker
pH: 8.50

| TIME | TEMP | n' | K' | Viscosity at Rates in Sec$^{-1}$ | | |
|---|---|---|---|---|---|---|
| | | | | 105s-1 | 85s-1 | 42s-1 |
| 34 | 199 | 0.647 | 25.919 | 501 | 540 | 693 |
| 65 | 199 | 0.676 | 18.865 | 418 | 447 | 562 |
| 96 | 199 | 0.621 | 21.635 | 371 | 402 | 525 |
| 127 | 199 | 0.592 | 21.943 | 329 | 358 | 478 |
| 155 | 199 | 0.579 | 21.185 | 299 | 326 | 439 |
| 185 | 199 | 0.661 | 13.478 | 278 | 299 | 380 |
| 216 | 199 | 0.648 | 13.356 | 260 | 280 | 358 |
| 247 | 199 | 0.628 | 13.914 | 246 | 267 | 346 |
| 278 | 199 | 0.631 | 12.953 | 233 | 251 | 326 |
| 308 | 199 | 0.633 | 12.231 | 222 | 240 | 310 |
| 339 | 199 | 0.656 | 10.562 | 213 | 229 | 292 |
| 370 | 199 | 0.654 | 10.145 | 203 | 218 | 278 |
| 401 | 199 | 0.665 | 9.402 | 198 | 212 | 269 |
| 432 | 199 | 0.654 | 9.439 | 189 | 203 | 259 |
| 463 | 199 | 0.685 | 7.614 | 176 | 188 | 235 |
| 494 | 199 | 0.689 | 7.154 | 168 | 180 | 224 |
| 525 | 199 | 0.705 | 6.622 | 168 | 179 | 220 |
| 556 | 199 | 0.701 | 6.685 | 166 | 177 | 219 |
| 586 | 199 | 0.680 | 6.899 | 156 | 166 | 209 |
| 617 | 199 | 0.707 | 5.938 | 152 | 162 | 199 |
| 627 | 199 | 0.737 | 5.131 | 151 | 160 | 192 |
| 658 | 199 | 0.724 | 5.288 | 146 | 155 | 188 |

TABLE 8-continued

Temperature (°F.): 200
Additives: 2% KCl, 4.8 gr. guar gum, 0.3 gr. Na$_2$S$_2$O$_3$.5H$_2$O,
0.5 ml 45% (wt) K$_2$CO$_3$ and 0.25 ml of diluted crosslinker
pH: 8.50

| TIME | TEMP | n' | K' | Viscosity at Rates in Sec$^{-1}$ | | |
|---|---|---|---|---|---|---|
| | | | | 105s-1 | 85s-1 | 42s-1 |
| 689 | 199 | 0.682 | 5.982 | 136 | 146 | 182 |
| 720 | 199 | 0.702 | 5.371 | 134 | 143 | 176 |
| 751 | 199 | 0.727 | 4.707 | 132 | 140 | 170 |
| 781 | 199 | 0.709 | 4.917 | 127 | 135 | 166 |
| 812 | 199 | 0.686 | 5.280 | 122 | 131 | 163 |
| 843 | 199 | 0.718 | 4.305 | 116 | 123 | 150 |
| 874 | 199 | 0.689 | 4.7115 | 111 | 118 | 147 |
| 905 | 199 | 0.732 | 3.831 | 110 | 116 | 141 |
| 936 | 199 | 0.675 | 4.9115 | 108 | 116 | 146 |
| 967 | 199 | 0.73 | 3.7031 | 105 | 112 | 135 |
| 998 | 199 | 0.695 | 4.31 | 104 | 111 | 138 |
| 1028 | 85 | 0.464 | 32.3876 | 267 | 299 | 437 |

Example 10

In this example, a liter of 2%(wt/vol) aqueous potassium chloride was vigorously stirred while adding 4.8 gr of fracturing fluid quality hydroxypropyl guar (HPG), a derivatized guar gum and 1.2 gr of sodium bicarbonate. After adequate dispersing, the stirring rate was slowed and the polymer was allowed to hydrate for about an hour.

A 250 ml aliquot was withdrawn and treated with 0.3 gr of sodium thiosulfate and 0.08 ml of 45% potassium carbonate. Then, with vigorous stirring, 0.12 ml of crosslinker prepared in Example 1 was added to the sol. The sol pH was 9.04 and the data acquired from the rheological evaluation at 250° F. is presented in Table 9.

TABLE 9

Temperature (°F.): 250
Additives: 2% KCl, 4.8 gr. HPG, 1.2 gr. NaHCO$_3$, 0.3 gr. Na$_2$S$_2$O$_3$.5H$_2$O,
0.08 ml 45% (wt) K$_2$CO$_3$ and 0.12 ml crosslinker
pH: 9.04

| TIME | TEMP | n' | K' | Viscosity at Rates in Sec$^{-1}$ | | |
|---|---|---|---|---|---|---|
| | | | | 105s-1 | 85s-1 | 42s-1 |
| 32 | 248 | 0.675 | 16.072 | 354 | 379 | 477 |
| 61 | 249 | 0.580 | 20.483 | 290 | 317 | 426 |
| 89 | 249 | 0.629 | 15.632 | 278 | 301 | 391 |
| 118 | 249 | 0.577 | 17.076 | 238 | 261 | 351 |
| 145 | 249 | 0.617 | 13.297 | 224 | 243 | 318 |
| 173 | 249 | 0.565 | 15.686 | 207 | 227 | 309 |
| 202 | 249 | 0.581 | 13.393 | 191 | 208 | 280 |
| 231 | 249 | 0.571 | 12.945 | 176 | 192 | 260 |
| 260 | 249 | 0.586 | 11.859 | 173 | 188 | 252 |
| 289 | 249 | 0.592 | 11.005 | 165 | 180 | 239 |
| 318 | 249 | 0.661 | 7.727 | 160 | 171 | 218 |
| 347 | 249 | 0.599 | 9.329 | 144 | 157 | 208 |
| 376 | 249 | 0.596 | 9.236 | 141 | 153 | 204 |
| 405 | 249 | 0.650 | 6.918 | 136 | 146 | 187 |
| 434 | 249 | 0.621 | 7.377 | 126 | 137 | 179 |
| 463 | 249 | 0.611 | 7.373 | 121 | 131 | 172 |
| 492 | 249 | 0.597 | 7.572 | 116 | 126 | 168 |
| 521 | 249 | 0.619 | 6.385 | 108 | 117 | 154 |
| 550 | 249 | 0.664 | 5.014 | 105 | 113 | 143 |
| 579 | 249 | 0.689 | 4.331 | 102 | 109 | 135 |
| 608 | 249 | 0.654 | 4.854 | 97 | 104 | 133 |
| 616 | 249 | 0.629 | 5.273 | 94 | 101 | 132 |
| 645 | 249 | 0.613 | 5.329 | 88 | 95 | 125 |

TABLE 9-continued

Temperature (°F.): 250
Additives: 2% KCl, 4.8 gr. HPG, 1.2 gr. NaHCO$_3$, 0.3 gr. Na$_2$S$_2$O$_3$.5H$_2$O,
0.08 ml 45% (wt) K$_2$CO$_3$ and 0.12 ml crosslinker
pH: 9.04

| TIME | TEMP | n' | K' | Viscosity at Rates in Sec$^{-1}$ | | |
|---|---|---|---|---|---|---|
| | | | | 105s-1 | 85s-1 | 42s-1 |
| 674 | 249 | 0.663 | 4.124 | 86 | 92 | 117 |
| 703 | 249 | 0.689 | 3.751 | 88 | 94 | 117 |
| 732 | 249 | 0.661 | 4.005 | 83 | 89 | 113 |
| 761 | 249 | 0.675 | 3.766 | 83 | 89 | 112 |
| 790 | 249 | 0.698 | 3.294 | 81 | 86 | 107 |
| 819 | 249 | 0.702 | 3.119 | 78 | 83 | 102 |
| 848 | 249 | 0.688 | 3.2253 | 76 | 81 | 100 |
| 877 | 249 | 0.686 | 3.1348 | 73 | 78 | 97 |
| 906 | 249 | 0.706 | 2.8311 | 72 | 77 | 94 |
| 935 | 249 | 0.691 | 3.0418 | 72 | 77 | 96 |
| 964 | 249 | 0.662 | 3.236 | 67 | 72 | 91 |
| 993 | 250 | 0.643 | 3.4503 | 66 | 71 | 91 |
| 1022 | 249 | 0.657 | 3.1647 | 64 | 69 | 88 |
| 1051 | 249 | 0.657 | 3.0802 | 62 | 67 | 85 |
| 1080 | 249 | 0.663 | 2.9762 | 62 | 67 | 84 |
| 1109 | 249 | 0.64 | 3.2035 | 60 | 65 | 83 |
| 1137 | 100 | 0.511 | 19.5655 | 201 | 223 | 315 |

Example 11

In this example, a 250 ml aliquot of CMHPG prepared as described in Example 7 was treated with 0.3 gr of sodium thiosulfate. Then, with stirring, acetic acid was added dropwise until the sol pH was 5.70. Lastly, with vigorous stirring of the sol, 0.19 ml of crosslinker prepared in Example 1 was added. The final sol pH was 5.70 and the data obtained from the rheological evaluation at 200° F. are presented in Table 10.

TABLE 10

Temperature (°F.): 200
Additives: 2% KCl, 4.8 gr. CMHPG, 0.3 gr. Na$_2$S$_2$O$_3$.5H$_2$O,
acetic acid added to adjust pH, and 0.19 ml crosslinker
pH: 5.70

| TIME | TEMP | n' | K' | Viscosity at Rates in Sec$^{-1}$ | | |
|---|---|---|---|---|---|---|
| | | | | 105s-1 | 85s-1 | 42s-1 |
| 32 | 205 | 0.444 | 70.514 | 530 | 596 | 883 |
| 61 | 202 | 0.455 | 70.838 | 561 | 629 | 924 |
| 90 | 202 | 0.435 | 76.512 | 552 | 622 | 926 |
| 118 | 202 | 0.425 | 78.281 | 539 | 608 | 913 |
| 147 | 202 | 0.434 | 74.248 | 533 | 601 | 895 |
| 176 | 202 | 0.446 | 68.372 | 519 | 583 | 862 |
| 205 | 202 | 0.466 | 61.856 | 515 | 577 | 841 |
| 234 | 202 | 0.441 | 65.286 | 484 | 545 | 808 |
| 263 | 202 | 0.454 | 59.014 | 465 | 522 | 767 |
| 292 | 202 | 0.444 | 58.220 | 438 | 492 | 729 |

Example 12

In this example, a 250 ml aliquot of CMHPG prepared as described in Example 7 was treated with 0.3 gr of sodium thiosulfate and 0.06 ml of 45%(wt) potassium carbonate. Then, with vigorous stirring of the sol, 0.15 ml of crosslinker prepared in Example 1 was added.

The final sol pH was 9.00 and the data acquired from the rheological evaluation at 275° F. are shown in Table 11.

TABLE 11

Temperature (°F.): 275
Additives: 2% KCl, 4.8 gr. CMHPG, 0.3 gr. Na$_2$S$_2$O$_3$.5H$_2$O, 0.06 ml 45% (wt) K$_2$CO$_3$ and 0.15 ml crosslinker
pH: 9.00

| TIME | TEMP | n' | K' | Viscosity at Rates in Sec$^{-1}$ | | |
|---|---|---|---|---|---|---|
| | | | | 105s-1 | 85s-1 | 42s-1 |
| 31 | 274 | 0.622 | 47.012 | 809 | 877 | 1145 |
| 60 | 274 | 0.564 | 48.740 | 641 | 703 | 955 |
| 89 | 274 | 0.533 | 44.902 | 511 | 564 | 784 |
| 118 | 274 | 0.510 | 41.733 | 427 | 473 | 668 |
| 147 | 274 | 0.546 | 31.878 | 385 | 424 | 584 |
| 176 | 274 | 0.498 | 36.050 | 349 | 388 | 552 |
| 205 | 275 | 0.522 | 30.511 | 330 | 365 | 511 |
| 234 | 275 | 0.535 | 25.977 | 298 | 329 | 457 |
| 263 | 274 | 0.516 | 26.552 | 279 | 309 | 435 |
| 292 | 274 | 0.571 | 18.883 | 256 | 281 | 380 |
| 321 | 274 | 0.558 | 20.908 | 267 | 293 | 401 |
| 350 | 274 | 0.542 | 21.471 | 255 | 281 | 388 |
| 379 | 274 | 0.548 | 19.449 | 237 | 261 | 359 |
| 408 | 274 | 0.532 | 19.154 | 217 | 239 | 333 |
| 437 | 273 | 0.569 | 15.422 | 207 | 227 | 308 |
| 466 | 274 | 0.598 | 12.429 | 191 | 208 | 277 |
| 495 | 274 | 0.527 | 15.677 | 173 | 192 | 268 |
| 524 | 274 | 0.505 | 15.872 | 159 | 176 | 250 |
| 553 | 274 | 0.544 | 12.159 | 146 | 160 | 221 |
| 582 | 274 | 0.535 | 11.503 | 132 | 146 | 202 |
| 610 | 274 | 0.559 | 9.375 | 120 | 132 | 180 |
| 639 | 274 | 0.520 | 10.076 | 108 | 119 | 168 |
| 668 | 274 | 0.566 | 7.544 | 100 | 110 | 149 |
| 697 | 274 | 0.567 | 6.818 | 91 | 100 | 135 |
| 726 | 274 | 0.533 | 7.229 | 82 | 91 | 126 |
| 755 | 274 | 0.562 | 5.840 | 76 | 83 | 114 |
| 773 | 274 | 0.581 | 5.025 | 71 | 78 | 105 |
| 802 | 274 | 0.607 | 4.143 | 67 | 72 | 95 |
| 831 | 273 | 0.558 | 4.847 | 62 | 68 | 93 |
| 860 | 274 | 0.554 | 4.5336 | 57 | 63 | 86 |
| 889 | 273 | 0.565 | 4.123 | 54 | 60 | 81 |
| 918 | 274 | 0.574 | 3.7038 | 51 | 56 | 75 |
| 947 | 273 | 0.528 | 4.1565 | 46 | 51 | 71 |
| 976 | 274 | 0.581 | 3.0997 | 44 | 48 | 65 |

Example 13

In this example, a 250 ml aliquot of CMHPG prepared as described in Example 7 was treated with 0.3 gr of sodium thiosulfate and 0.06 ml of 45%(wt) potassium carbonate. Then, with vigorous stirring of the sol, 0.18 ml of crosslinker prepared in Example 1 was added. The final sol pH was 8.95 and the data acquired from the rheological evaluation at 300° F. are shown in Table 12.

TABLE 12

Temperature (°F.): 300
Additives: 2% KCl, 4.8 gr. CMHPG, 0.3 gr. Na$_2$S$_2$O$_3$.5H$_2$O, 0.06 ml 45% (wt) K$_2$CO$_3$ and 0.18 ml crosslinker
pH: 8.95

| TIME | TEMP | n' | K' | Viscosity at Rates in Sec$^{-1}$ | | |
|---|---|---|---|---|---|---|
| | | | | 105s-1 | 85s-1 | 42s-1 |
| 30 | 305 | 0.728 | 29.502 | 832 | 881 | 1067 |
| 59 | 284 | 0.624 | 31.910 | 555 | 600 | 783 |
| 88 | 298 | 0.571 | 30.819 | 419 | 458 | 620 |
| 117 | 299 | 0.539 | 28.911 | 338 | 373 | 516 |
| 146 | 299 | 0.537 | 24.060 | 279 | 308 | 426 |
| 175 | 299 | 0.553 | 18.374 | 229 | 252 | 346 |
| 204 | 299 | 0.568 | 13.462 | 180 | 198 | 268 |

TABLE 12-continued

Temperature (°F.): 300
Additives: 2% KCl, 4.8 gr. CMHPG, 0.3 gr. Na$_2$S$_2$O$_3$.5H$_2$O, 0.06 ml 45% (wt) K$_2$CO$_3$ and 0.18 ml crosslinker
pH: 8.95

| TIME | TEMP | n' | K' | Viscosity at Rates in Sec$^{-1}$ | | |
|---|---|---|---|---|---|---|
| | | | | 105s-1 | 85s-1 | 42s-1 |
| 233 | 299 | 0.581 | 9.721 | 138 | 151 | 203 |
| 262 | 298 | 0.584 | 7.375 | 106 | 116 | 156 |
| 291 | 299 | 0.618 | 4.815 | 81 | 88 | 115 |
| 320 | 299 | 0.602 | 3.859 | 61 | 66 | 87 |
| 349 | 298 | 0.619 | 2.809 | 48 | 52 | 68 |
| 378 | 298 | 0.630 | 2.125 | 38 | 41 | 53 |
| 407 | 298 | 0.552 | 2.526 | 31 | 35 | 47 |
| 436 | 299 | 0.401 | 4.026 | 25 | 28 | 43 |
| 465 | 299 | 0.314 | 5.343 | 22 | 25 | 41 |
| 493 | 298 | 0.438 | 2.767 | 20 | 23 | 34 |
| 522 | 298 | 0.445 | 2.493 | 19 | 21 | 31 |
| 551 | 298 | 0.438 | 2.344 | 17 | 19 | 29 |
| 580 | 298 | 0.518 | 1.456 | 15 | 17 | 24 |
| 609 | 298 | 0.606 | 0.833 | 13 | 14 | 19 |
| 638 | 298 | 0.667 | 0.556 | 12 | 13 | 16 |
| 667 | 299 | 0.619 | 0.615 | 10 | 11 | 15 |
| 696 | 298 | 0.446 | 1.166 | 9 | 10 | 15 |
| 725 | 298 | 0.397 | 1.347 | 8 | 9 | 14 |
| 754 | 298 | 0.263 | 2.300 | 7 | 9 | 15 |
| 783 | 298 | 0.218 | 2.649 | 7 | 8 | 14 |
| 812 | 298 | 0.207 | 2.680 | 7 | 8 | 14 |
| 841 | 298 | 0.161 | 3.2311 | 7 | 8 | 14 |
| 851 | 298 | 0.197 | 2.7087 | 6 | 8 | 13 |
| 880 | 298 | 0.231 | 2.2448 | 6 | 7 | 13 |
| 909 | 298 | 0.088 | 4.2004 | 6 | 7 | 14 |
| 938 | 298 | 0.155 | 3.0535 | 6 | 7 | 13 |
| 967 | 298 | 0.208 | 2.515 | 6 | 7 | 13 |
| 995 | 298 | 0.167 | 2.9336 | 6 | 7 | 13 |
| 1024 | 298 | 0.158 | 2.8262 | 6 | 7 | 12 |
| 1053 | 298 | 0.194 | 2.4537 | 6 | 7 | 12 |
| 1082 | 298 | 0.13 | 3.2029 | 6 | 7 | 12 |
| 1111 | 297 | 0.174 | 2.6641 | 6 | 7 | 12 |
| 1140 | 297 | 0.198 | 2.281 | 5 | 6 | 11 |
| 1169 | 298 | 0.162 | 2.6941 | 5 | 7 | 12 |
| 1198 | 297 | 0.093 | 3.8153 | 6 | 7 | 13 |
| 1227 | 298 | 0.119 | 3.4276 | 6 | 7 | 13 |

Example 14

In this example, another 250 ml aliquot was withdrawn from the stock solution prepared as described in Example 2. This sol was treated with 0.3 gr of sodium thiosulfate. Then acetic acid was added dropwise until the sol pH achieved 5.70. Lastly, with vigorous stirring of the sol, 0.38 ml of crosslinker prepared in Example 1 was added. The sol pH was 5.70 and the data from the rheological evaluation at 200° F. is presented in Table 13.

TABLE 13

Temperature (°F.): 200
Additives: 2% KCl, 4.8 gr. guar gum, 0.3 gr. Na$_2$S$_2$O$_3$.5H$_2$O, acetic acid to adjust pH and 0.38 ml crosslinker
pH: 5.70

| TIME | TEMP | n' | K' | Viscosity at Rates in Sec$^{-1}$ | | |
|---|---|---|---|---|---|---|
| | | | | 105s-1 | 85s-1 | 42s-1 |
| 32 | 200 | 0.546 | 25.628 | 310 | 341 | 470 |
| 61 | 202 | 0.552 | 22.357 | 278 | 306 | 419 |
| 89 | 202 | 0.563 | 20.055 | 262 | 288 | 392 |
| 118 | 202 | 0.625 | 14.912 | 260 | 282 | 367 |

TABLE 13-continued

Temperature (°F.): 200
Additives: 2% KCl, 4.8 gr. guar gum, 0.3 gr. $Na_2S_2O_3 \cdot 5H_2O$,
acetic acid to adjust pH and 0.38 ml crosslinker
pH: 5.70

| TIME | TEMP | n' | K' | Viscosity at Rates in $Sec^{-1}$ | | |
|---|---|---|---|---|---|---|
| | | | | 105s-1 | 85s-1 | 42s-1 |
| 147 | 202 | 0.529 | 21.147 | 236 | 261 | 364 |
| 176 | 202 | 0.550 | 17.726 | 218 | 240 | 330 |
| 205 | 202 | 0.567 | 15.597 | 208 | 228 | 309 |
| 234 | 202 | 0.559 | 15.232 | 196 | 215 | 293 |
| 262 | 202 | 0.589 | 12.378 | 183 | 199 | 266 |
| 291 | 202 | 0.626 | 9.481 | 166 | 180 | 234 |

Example 15

Another 250 ml aliquot of sol described in Example 2 was treated with 0.30 gr sodium thiosulfate and 0.38 ml of 45%(wt) potassium carbonate. Then, 0.12 ml of crosslinker described in Example 1 was added to the vigorously stirred sol. The sol pH was 8.50 and the rheological data obtained at 275° F. is presented in Table 14.

TABLE 14

Temperature (°F.): 275
Additives: 2% KCl, 4.8 gr. guar gum, 0.30 gr. $Na_2S_2O_3 \cdot 5H_2O$,
0.38 ml 45% (wt) $K_2CO_3$ and 0.12 ml crosslinker
pH: 8.50

| TIME | TEMP | n' | K' | Viscosity at Rates in $Sec^{-1}$ | | |
|---|---|---|---|---|---|---|
| | | | | 105s-1 | 85s-1 | 42s-1 |
| 32 | 271 | 0.603 | 21.522 | 339 | 369 | 488 |
| 61 | 272 | 0.575 | 20.274 | 280 | 307 | 414 |
| 90 | 273 | 0.595 | 14.999 | 228 | 248 | 330 |
| 119 | 273 | 0.652 | 10.192 | 202 | 217 | 278 |
| 148 | 273 | 0.659 | 8.537 | 175 | 188 | 239 |
| 177 | 273 | 0.692 | 6.438 | 154 | 164 | 204 |
| 206 | 273 | 0.683 | 5.891 | 135 | 144 | 180 |
| 235 | 273 | 0.762 | 3.680 | 122 | 128 | 151 |
| 264 | 273 | 0.720 | 4.060 | 110 | 117 | 143 |
| 293 | 273 | 0.725 | 3.473 | 97 | 102 | 124 |
| 322 | 273 | 0.652 | 4.396 | 87 | 94 | 120 |
| 351 | 273 | 0.663 | 3.688 | 77 | 83 | 105 |
| 380 | 272 | 0.724 | 2.731 | 76 | 80 | 97 |
| 408 | 273 | 0.673 | 3.063 | 67 | 72 | 90 |

When using the zirconium compounds of the invention as crosslinking agents for aqueous polymer gels used as fracturing fluids, a gelled polymer fracturing fluid is first prepared by adding between about 1% or less by weight of a soluble polymer such as guar, guar derivative or carboxylated cellulose to water. The zirconium crosslinking agent is then added to the gelled fluid in solution while mixing. The amount of the crosslinking agent used to carry out the method of the invention will vary over a wide range and therefore the amounts will vary according to the formation being treated. Preferably, the amount of crosslinking agent used will be in the range from about 0.005 to in excess of 1.00 weight percent, most preferably about 0.01 to 0.10 weight percent, based on the total weight of aqueous fluid. Additionally, proppants and other additives, such as gel stabilizers, buffers, crosslink delaying agents and surfactants, may be added to the fluid prior to pumping into an oil or gas well. The fluid is then pumped into the well at a sufficiently high rate or pressure to cause fractures within the hydrocarbon bearing areas of the formation. The zirconium compound is particularly useful when treating high temperature wells, i.e. those having temperatures in excess of 200° F., due to the good thermal stability and retained viscosity of the crosslinked polymer gel.

An invention has been provided with several advantages. The method of the invention allows organo-zirconium compounds to be formed without producing undesirable by-products that must be removed by washing and filtering procedures. Because zirconium carbonate is used as the starting material, the reaction results in the production of carbon dioxide gas as a by-product. The carbon dioxide merely bubbles from solution as a gas so that no additional separating techniques are required. This eliminates the loss of product that would otherwise occur during the washing and filtering steps. There is also no chloride to be recovered and disposed of. The novel organo-zirconium compounds of the invention overcome many of the disadvantages of the prior art compounds, such as high cost, as well as being more applicable for guar gums utilized in aqueous based fracturing fluids.

While the invention has been shown in only one of its forms, it should be apparent to those skilled in the art that it is not so limited but is susceptible to various changes without departing from the scope of the invention.

I claim:

1. A method of formulating an organo-zirconium compound comprising:

combining in solution an amount of an aldehyde or dialdehyde with an amount of a zirconium salt and allowing the solution to react.

2. The method of claim 1, wherein:

wherein the aldehyde or dialdehyde is selected from the group consisting of dialdehydes having about 2–4 carbon atoms, keto aldehydes having about 3–4 carbon atoms, hydroxyl aldehydes having 2–4 carbon atoms, ortho substituted aromatic dialdehydes and ortho substituted aromatic hydroxyl aldehydes.

3. A method of formulating an organo-zirconium compound comprising combining in solution an amount of glyoxal with an amount of zirconium carbonate and allowing the combined solution to react.

4. A method of formulating an organo-zirconium compound comprising:

combining in solution an amount of an aldehyde or dialdehyde with an amount of a zirconium salt:

allowing the combined solution to react;

wherein carbon dioxide is formed as a by-product of the reacting solution; and allowing the carbon dioxide to evolve as a gas from the solution.

5. The method of claim 1, further comprising:

heating the solution to a temperature of at least about 200° F.

6. The method of claim 3, wherein:

the amount of zirconium ion combined with glyoxal is in a molar ratio from about 1:0.5 to 1:20.

7. The method of claim 3, wherein:

the amount of zirconium ion combined with glyoxal is in a molar ratio of about 1:2.5 to 1:7.

8. The method of claim 1, wherein:

the reacting solution is kept at a pH below about 6.

9. The method of claim 1, further comprising:

neutralizing the solution after the reaction is complete.

10. A method of formulating zirconium compound comprising:

preparing an aqueous solution of glyoxal, heating the solution to a temperature of at least 200° F., then admixing to the solution an amount of zirconium carbonate and allowing the solution to react to form a precipitate of the zirconium compound and carbon dioxide gas, and allowing the carbon dioxide gas to evolve from the solution.

11. The method of claim 10, wherein:

the amount of zirconium ion combined with glyoxal is in a molar ratio from about 1:0.5 to 1:20.

12. The method of claim 10, wherein:

the amount of zirconium ion combined with glyoxal is in a molar ratio of about 1:2.5 to 1:7.

13. The method of claim 10, wherein:

the reacting solution is kept at a pH below about 6.

14. The method of claim 10, further comprising:

neutralizing the solution after the reaction is complete so that the precipitate is dissolved.

15. The method of claim 14, wherein:

the solution is neutralized by addition of an alkali metal hydroxide.

16. The method of claim 15, wherein:

the alkali metal hydroxide is selected from the group consisting of potassium hydroxide and sodium hydroxide.

17. The method of claim 16, wherein:

the alkali metal hydroxide is added in an amount of about 3 moles per mole of zirconium ion.

18. A method of preparing a zirconium crosslinker for use in crosslinking viscous polymer gels comprising the steps of:

combining in solution an amount of an aldehyde or dialdehyde with an amount of a zirconium salt and allowing the solution to react to form a precipitate of the zirconium compound and carbon dioxide gas, and allowing the carbon dioxide gas to evolve from the solution;

neutralizing the combined solution after the reaction is complete so that the precipitate is dissolved.

19. The method of claim 18, wherein:

the zirconium salt is zirconium carbonate and the aldehyde or dialdehyde is glyoxal.

20. The method of claim 19, wherein:

the amount of zirconium ion combined with glyoxal is in a molar ratio from about 1:0.5 to 1:20.

21. The method of claim 20, wherein:

the amount of zirconium ion combined with glyoxal is in a molar ratio of about 1:2.5 to 1:7.

22. The method of claim 18, wherein:

the reacting solution is kept at a pH below about 6.

23. The method of claim 18, further comprising:

the solution is neutralized by addition of an alkali metal hydroxide.

24. A method according to claim 18, wherein the viscous polymer gels comprise fracturing fluids for use in oil and gas wells.

25. A method according to claim 18, wherein the aldehyde or dialdehyde is selected from the group consisting of dialdehydes having about 2–4 carbon atoms, hydroxyl aldehydes having 2–4 carbon atoms, ortho substituted aromatic dialdehydes and ortho substituted aromatic hydroxyl aldehydes.

26. A method according to claim 3 or 4, further comprising heating the combined solution to a temperature of at least about 200° F.

27. The method according to claim 4, wherein the amount of zirconium ion combined with glyoxal is in a molar ration from about 1:0.5 to 1:20.

28. The method according to claim 4, wherein the amount of zirconium ion combined with glyoxal is in a molar ration of about 1:2.5 to 1:7.

29. The method according to claim 3 or 4, wherein the reacting solution is kept at a pH below about 6.

30. The method according to claim 4, further comprising neutralizing the solution after the reaction is complete.

31. The method according to claim 4, wherein:

the aldehyde or dialdehyde is selected from the group consisting of dialdehydes having about 2–4 carbon atoms, keto aldehydes having about 3–4 carbon atoms, hydroxyl aldehydes having 2–4 carbon atoms, ortho substituted aromatic dialdehydes and ortho substituted aromatic hydroxyl aldehydes.

* * * * *

UNITED STATES PATENT AND TRADEMARK OFFICE
CERTIFICATE OF CORRECTION

PATENT NO. : 5,773,638
DATED : June 30, 1998
INVENTOR(S) : Jeffrey C. Dawson and Hoang Van Le It is certified that error appears in the above-identified patent and that said Letters Patent is hereby corrected as shown below:

Column 4, line 52, delete "Theological" and insert --rheological--.
Column 7, Table 5, line 12, delete "584" and insert --564--.

Signed and Sealed this

Eighth Day of September, 1998

Attest:

BRUCE LEHMAN

Attesting Officer        Commissioner of Patents and Trademarks